United States Patent
Karunasiri

(10) Patent No.: US 9,717,906 B2
(45) Date of Patent: Aug. 1, 2017

(54) SYSTEMS AND METHODS FOR MEASURING A CURRENT OUTPUT BY A CURRENT GENERATION CIRCUIT INCLUDED IN A COCHLEAR IMPLANT

(71) Applicant: ADVANCED BIONICS AG, Staefa (CH)

(72) Inventor: R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,025

(22) PCT Filed: Dec. 23, 2013

(86) PCT No.: PCT/US2013/077595
§ 371 (c)(1),
(2) Date: Mar. 22, 2016

(87) PCT Pub. No.: WO2015/099681
PCT Pub. Date: Jul. 2, 2015

(65) Prior Publication Data
US 2016/0213925 A1 Jul. 28, 2016

(51) Int. Cl.
*A61N 1/36* (2006.01)

(52) U.S. Cl.
CPC .................. *A61N 1/36032* (2013.01)

(58) Field of Classification Search
None
See application file for complete search history.

(56) References Cited

U.S. PATENT DOCUMENTS

| 6,175,767 B1* | 1/2001 | Doyle, Sr. .......... A61N 1/36032 607/57 |
| 6,289,246 B1* | 9/2001 | Money .................. A61N 1/378 607/12 |
| 6,810,289 B1* | 10/2004 | Shaquer ............... H04R 25/606 607/137 |

(Continued)

FOREIGN PATENT DOCUMENTS

EP    0229449    7/1987

OTHER PUBLICATIONS

Partial International Search Report received in International Application No. PCT/US13/077595, dated Mar. 7, 2014.

(Continued)

*Primary Examiner* — Brian T Gedeon
(74) *Attorney, Agent, or Firm* — ALG Intellectual Property, LLC

(57) ABSTRACT

An exemplary system may include a sound processor that is communicatively coupled to a cochlear implant implanted within a patient. The cochlear implant may include a current generation circuit (402) in series with a capacitor (418) and a voltage measurement circuit (422). The sound processor may 1) direct the cochlear implant to enable the current generation circuit for a time interval, causing a current to flow to the capacitor, 2) direct the cochlear implant to use the voltage measurement circuit to measure a voltage change across the capacitor that occurs during the time interval, and 3) determine a current level of the current that flows from the current generation circuit to the capacitor. A corresponding method is also described.

20 Claims, 6 Drawing Sheets

(56) References Cited

U.S. PATENT DOCUMENTS

| | | | |
|---|---|---|---|
| 7,809,437 B2* | 10/2010 | Palmer | A61N 1/37 607/2 |
| 8,886,322 B2* | 11/2014 | Meadows | A61N 1/025 607/17 |
| 9,008,787 B2* | 4/2015 | Carter | A61N 1/36032 607/13 |
| 2011/0077698 A1 | 3/2011 | Tsampazis et al. | |
| 2012/0191146 A1 | 7/2012 | Markey et al. | |
| 2012/0316620 A1 | 12/2012 | Suaning et al. | |

OTHER PUBLICATIONS

International Search Report and Written Opinion received in International Application No. PCT/US13/077595, dated Jun. 20, 2014.

\* cited by examiner

SYSTEMS AND METHODS FOR MEASURING A CURRENT OUTPUT BY A CURRENT GENERATION CIRCUIT INCLUDED IN A COCHLEAR IMPLANT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

In a typical cochlear implant system, the electrical stimulation used to stimulate auditory nerve fibers is generated by one or more current sources included in a cochlear implant. For example, a pair of current sources (e.g., a positive current source and a negative current source) may be used to generate stimulation current (e.g., a biphasic stimulation pulse) that is applied to a particular electrode included in the cochlear implant system. Unfortunately, a current source included in a cochlear implant may not be precisely accurate due to variations in wafer process, layout, and design. In other words, the current source may not output the exact amount of current that it is commanded to output. A discrepancy in actual versus intended current output by a current source may result in various negative side effects including imbalanced biphasic stimulation pulses, a loss of compliance voltage to the current source, inaccuracies in the stimulation current provided to a patient, and/or unnecessary power consumption.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for measuring a current output by a current generation circuit included in a cochlear implant are described herein. As will be described in more detail below, a cochlear implant system may include a sound processor and a cochlear implant communicatively coupled to the sound processor. The cochlear implant may include a current generation circuit, a capacitor in series with the current generation circuit, and a voltage measurement circuit. The sound processor may 1) direct the cochlear implant to enable (i.e., turn on) the current generation circuit for a time interval, which may cause a current to flow from the current generation circuit to the capacitor during the time interval, 2) direct the cochlear implant to use the voltage measurement circuit to measure a voltage change across the capacitor that occurs during the time interval, and 3) determine a current level of the current that flows from the current generation circuit to the capacitor based on the measured voltage change across the capacitor and on the duration of the time interval.

The systems and methods described herein may be used to measure an accuracy of one or more current sources included in a cochlear implant before or after the cochlear implant is implanted within a patient. The measured accuracy may then be used to calibrate the one or more current sources so that the intended and actual currents output by the one or more current sources are the same. In this manner, the systems and methods described herein may ensure that precise stimulation levels are applied to the patient, conserve power, and improve overall cochlear implant system performance. Other benefits of the systems and methods described herein will be made apparent herein.

Figure 1:
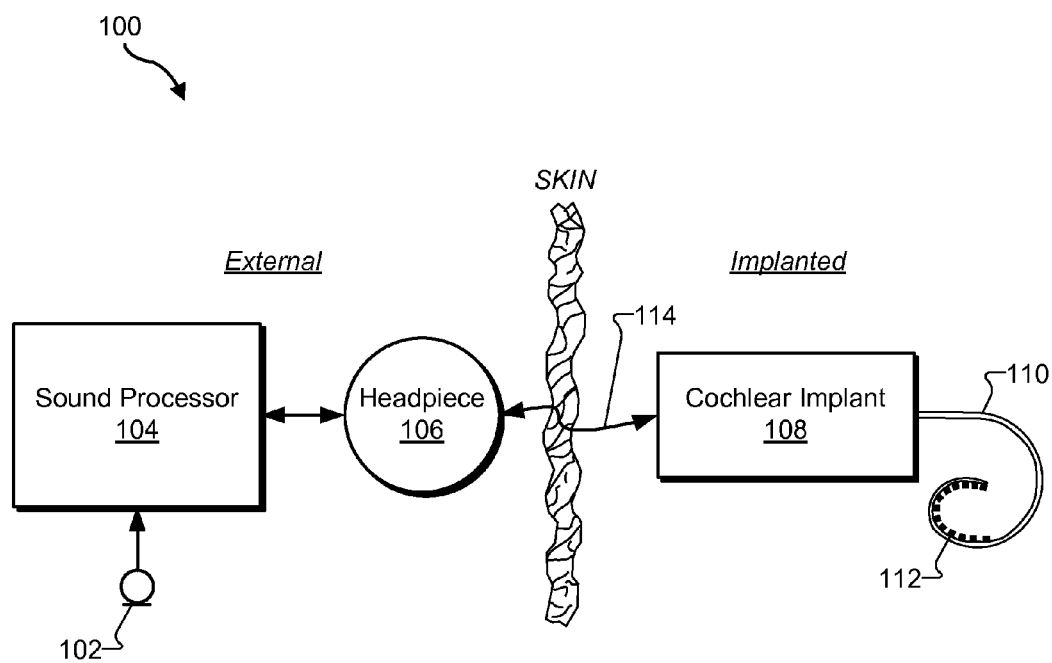
FIG. 1 illustrates an exemplary cochlear implant system according to principles described herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or RF power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or RF power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
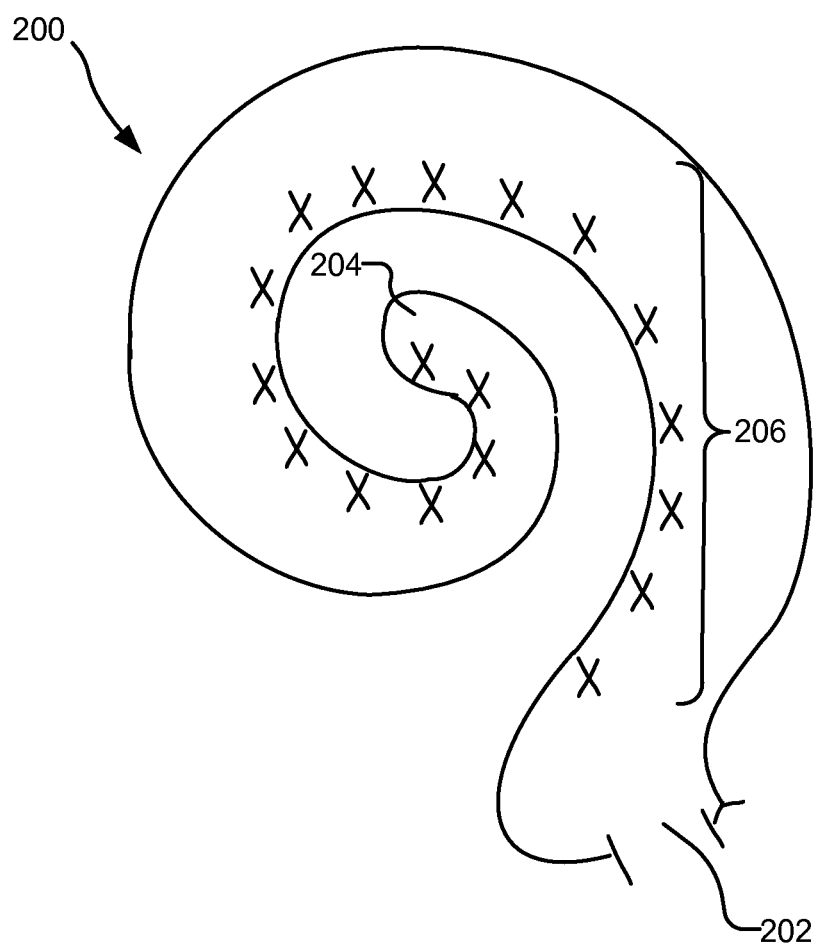
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
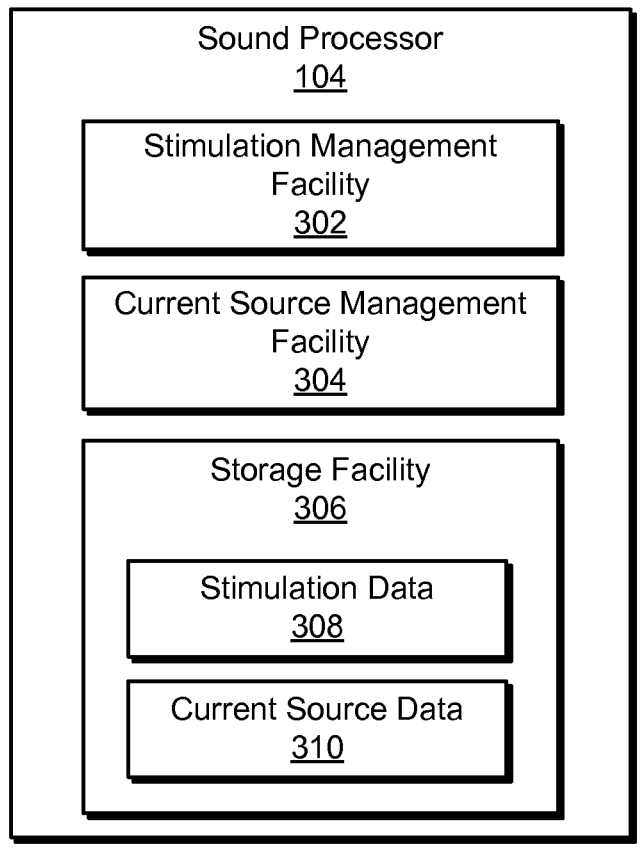
FIG. 3 illustrates exemplary components of a sound processor according to principles described herein.

FIG. 3 illustrates exemplary components of a sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a stimulation management facility 302, a current source management facility 304, and a storage facility 306, which may be in communication with one another using any suitable communication technologies. Storage facility 306 may be configured to maintain stimulation data 308 generated and/or used by stimulation management facility 302, and current source data 310 (e.g., data representative of one or more measured voltage changes) generated and/or used by current source management facility 304. Storage facility 306 may maintain additional or alternative data as may serve a particular implementation. One or more of facilities 302 through 306 may include a computing device or processor configured to perform one or more of the functions described herein. Facilities 302 through 306 will now be described in more detail.

Stimulation management facility 302 may be configured to perform various stimulation management operations with respect to an audio signal presented to a cochlear implant patient. For example, stimulation management facility 302 may receive an audio signal presented to a cochlear implant patient (e.g., during a normal operation of the cochlear implant system 100). Stimulation management facility 302 may then perform one or more pre-processing operations, spectral analysis operations, noise reduction operations, mapping operations, and/or any other types of signal processing operations with respect to the received audio signal as may serve a particular application.

Once the audio signal has been processed, stimulation management facility 302 may direct cochlear implant 108 to generate and apply stimulation current (e.g., an electrical stimulation pulse) representative of the audio signal by way of an electrode (e.g., one of electrodes 112) coupled to the cochlear implant 108. For example, stimulation management facility 302 may provide a command directing cochlear implant 108 (e.g., by way of a command signal from headpiece 106 via wireless communication link 114) to generate the stimulation current. The stimulation current may be generated by cochlear implant 108 in any suitable manner.

Current source management facility 304 may be configured to perform one or more current source management operations. For example, current source management facility 304 may measure current output by one or more current sources included in cochlear implant 108 in order to ensure that each of the one or more current sources is accurate. This and other current source management operations that may be performed by current source management facility 304 will be described in more detail below.

Figure 4:
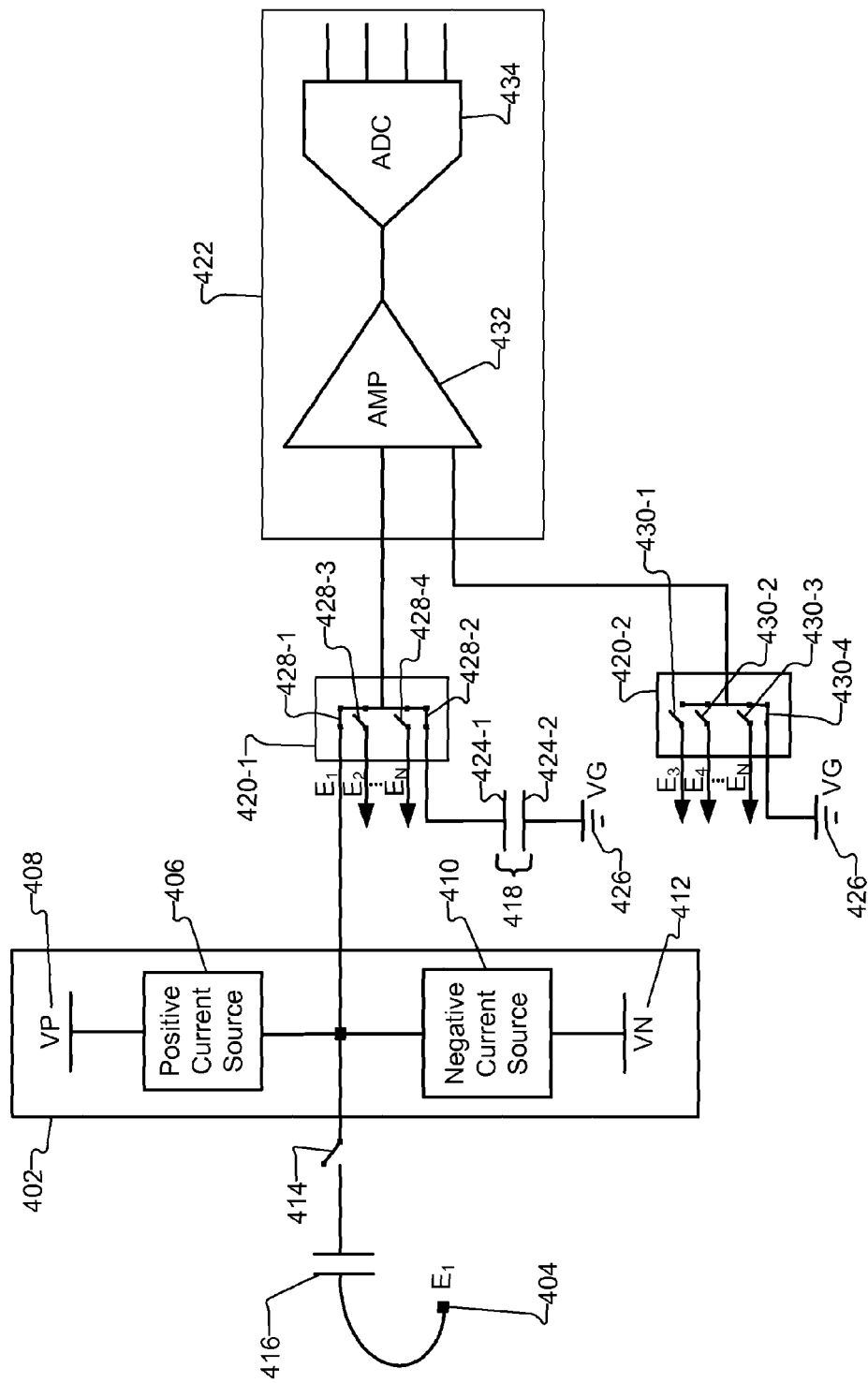
FIGS. 4-5 illustrate exemplary components of a cochlear implant according to the principles described herein.

FIG. 4 shows various components that may be included in cochlear implant 108. It will be recognized that the exemplary components shown in FIG. 4 are merely representative of the many different components that may be included in cochlear implant 108 and that cochlear implant 108 may include additional or alternative components as may serve a particular implementation. As shown in FIG. 4, cochlear implant 108 may include a current generation circuit 402 associated with a particular electrode 404 (labeled $E_1$ in FIG. 4) included in electrodes 112. A similar current generation circuit may be included within cochlear implant 108 for each of the other electrodes included in electrodes 112.

Current generation circuit 402 may include one or more current sources used to generate a current that may be applied to electrode 404. For example, as shown in FIG. 4, current generation circuit 402 may include a positive current source 406 tied to a positive voltage supply 408 (labeled "VP" in FIG. 4) and a negative current source 410 tied to a negative voltage supply 412 (labeled "VN" in FIG. 4). Together, positive current source 406 and negative current source 410 form a pair of current sources that may be used to generate biphasic stimulation pulses that are applied to electrode 404, for example. While two current sources 406 and 410 are shown to be included in current generation circuit 402, it will be recognized that in some alternative embodiments, only one current source is included in current generation circuit 402.

Current sources 406 and 410 may be connected to electrode 404 by way of an isolation switch 414 and a DC blocking capacitor 416. As will be described in more detail below, isolation switch 414 may be opened to prevent current from flowing to electrode 404 while an accuracy of current source 406 and/or current source 410 is being measured.

To facilitate measurement of an accuracy of one or more of the current sources 406 and 410 included in current generation circuit 402, cochlear implant 108 may include a capacitor 418, a first multiplexer ("MUX") 420-1, a second MUX 420-2, and a voltage measurement circuit 422. Each of these components will now be described.

Capacitor 418 may be implemented by any suitable capacitor (e.g., a precision capacitor). As shown, a first side 424-1 (e.g., a first conductive plate) of capacitor 418 may be coupled to an output of MUX 420-1 and a second side 424-2 (e.g., a second conductive plate) of capacitor 418 may be coupled to a reference voltage level 426 (labeled "VG" in FIG. 4). Reference voltage level 426 may be any suitable reference voltage level, such as a ground voltage or any other voltage level midway between positive voltage supply 408 and negative voltage supply 412.

As shown, MUX 420-1 is positioned in series between current generation circuit 402 and capacitor 418, and may be used to selectively connect capacitor 418 to the output of the current generation circuit 402 associated with electrode 404 (or to the output of any other current generation circuit associated with any other electrode (labeled $E_2$ through $E_N$) included in electrodes 112).

To facilitate selective connection of capacitor 418 to the output of a desired current generation circuit (e.g., current generation circuit 402), MUX 420-1 may include a plurality of switches 428 (e.g., switches 428-1 through 428-4). As shown, switch 428-1 corresponds to an input port of MUX 420-1 that is associated with current generation circuit 402, switch 428-2 corresponds to an output port of MUX 420-1 to which capacitor 418 is connected, switch 428-3 corresponds to an input port of MUX 420-1 that is associated with a current generation circuit associated with electrode $E_2$, etc.

Each switch 428 may be selectively (e.g., programmably) opened or closed in order to selectively connect capacitor 418 to the output of a desired current generation circuit. For example, FIG. 4 shows that switches 428-1 and 428-2 are closed and that switches 428-3 and 428-4 are open. In this configuration, capacitor 418 is connected to the output of current generation circuit 402. In other words, in this configuration, current output by current generation circuit 402 may flow through MUX 420-1 to capacitor 418.

MUX 420-2 may be configured to selectively provide the reference voltage level 426 as an input to voltage measurement circuit 422. MUX 420-2 may also be configured to selectively provide other reference voltage level associated with other electrodes included in electrodes 112 as an input to voltage measurement circuit 422. To this end, MUX 420-2 may include a plurality of switches 430 (e.g., switches 430-1 through 430-4). To provide reference voltage level 426 as an input to voltage measurement circuit 422, switch 430-4 is closed and the remaining switches 430 are open, as shown in FIG. 4.

Voltage measurement circuit 422 may be configured to measure a voltage change across the capacitor 418 that occurs during a particular time interval while one or more of current sources 406 and 410 are enabled. To this end, voltage measurement circuit 422 may include a differential amplifier 432 and an analog-to-digital converter ("ADC") 434. As shown, a first input of differential amplifier 432 may be connected to the first side 424-1 of capacitor 418 (e.g., at any point along a conductive path between the output of current generation circuit 402 and the first side 424-1 of the capacitor 418). A second input of differential amplifier 432 may be connected to the reference voltage level 426 (e.g., when switch 430-4 is closed). In this configuration, differential amplifier 432 may measure a voltage change across the capacitor 418 by determining a difference between a voltage level on the first side 424-1 of the capacitor 418 and a voltage level on the second side 424-2 of the capacitor 418, which, in this case, is the reference voltage level. ADC 434 may then convert the measured voltage change into a digital word representative of the measured voltage change.

Various ways in which the components shown in FIG. 4 may be used to measure the accuracy of current generation circuit 402 (e.g., positive current source 406 and/or negative current source 410) will now be described.

In some examples, to measure the accuracy of current generation circuit 402, current source management facility 304 may begin by measuring the current output by current generation circuit 402. To this end, current source management facility 304 may direct cochlear implant 108 to enable the current generation circuit 402 during a time interval, which may be set to be any suitable duration (e.g., a duration long enough for charge to build up on capacitor 418, but short enough to prevent capacitor 418 from becoming fully charged).

During the measurement procedure, current source management facility 304 may prevent the current output by current generation circuit 402 from flowing to electrode 404. This may be performed by ensuring that switch 414 is open during the time interval during which current generation circuit 402 is enabled. Current source management facility 304 may open switch 414 in any suitable manner. For example, current source management facility 304 may transmit a command to cochlear implant 108 that directs cochlear implant 108 to open switch 414.

Figure 5:
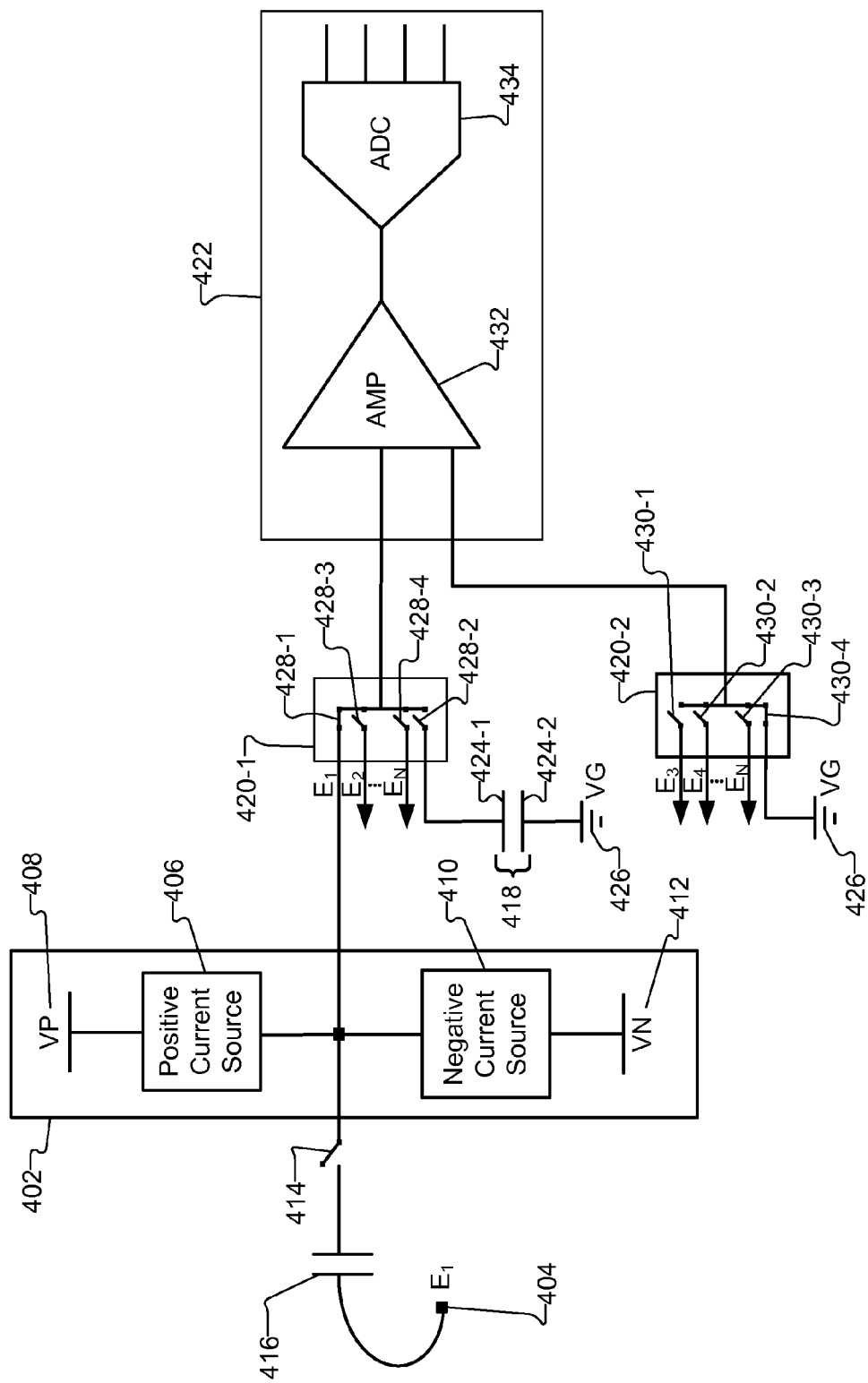

Current source management facility 304 may also ensure that the current output by current generation circuit 402 during the time interval flows to capacitor 418. This may be performed by directing cochlear implant 108 to close switches 428-1 and 428-2 (and open the remaining switches 428 in MUX 420-1) prior to or at the beginning of the time interval during which current generation circuit 402 is enabled. At the completion of the time interval, current source management facility 304 may disable current generation circuit 402 and/or open switch 428-1 to prevent current from flowing to capacitor 418. For example, FIG. 5 is similar to FIG. 4, but shows that switch 428-2 has been opened.

Current source management facility 304 may be further configured to direct cochlear implant 108 to use voltage measurement circuit 422 to measure a voltage change across the capacitor 418 that occurs during the time interval during which the current output by the current generation circuit 402 flows to the capacitor 418. This may be performed in any suitable manner. For example, as described above, current source management facility 304 may direct cochlear implant 108 to use voltage measurement circuit 422 (i.e., differential amplifier 432) to determine a difference between a voltage level on the first side 424-1 of capacitor 418 and a voltage level on the second side 424-2 of capacitor 418.

Voltage measurement circuit 422 (i.e., ADC 434) may convert the measured voltage change into a digital word representative of the measured voltage change. Communication circuitry (e.g., a transmitter) included in cochlear implant 108 may transmit the digital word representative of the measured voltage change to sound processor 108.

Current source management facility 304 may determine, based on the measured voltage change and on a duration of the time interval, a current level of the current that flows from the current generation circuit 402 to the capacitor 418. For example, the current level of the current output by the current generation circuit 402 may be represented computationally by c*dv/dt, where "c" is a value of the capacitor, "dv" is the measured voltage change, and "dt" is the duration of time interval. The value of the capacitor (e.g., the value in picofarads) may be stored within sound processor 108 (e.g., as current source data 310) or otherwise accessed by current source management facility 304. Hence, current source management facility 304 may determine the current level of the current that flows from the current generation circuit 402 to the capacitor 418 by computing c*dv/dt.

The measured current level may then be used to determine an accuracy of current generation circuit 402 and/or to perform one or more operations configured to compensate for the inaccuracy of current generation circuit 402. For example, current source management facility 304 may use the measured current level to calibrate current generation circuit 402.

As an example, the systems and methods described herein may be used to determine whether positive and negative current sources 406 and 410 are mismatched (i.e., if they output slightly different current levels). To this end, current source management facility 304 may direct cochlear implant 108 to concurrently enable positive current source 406 and negative current source 410 for a time interval, which may be set to be any suitable duration (e.g., an amount of time sufficient for charge to build up on capacitor 418). This may be performed in any suitable manner. For example, current source management facility 304 may direct positive current source 406 and negative current source 410 to output current equal in amplitude and opposite in phase. To illustrate, current source management facility 304 may provide a command (e.g., in the form of a control word transmitted to cochlear implant 108) for positive current source 406 to output positive 50 microamps of current and negative current source 410 to output negative 50 microamps of current.

If the positive and negative current sources 406 and 410 are mismatched, the output of current generation circuit 402 during the time interval is a mismatch current equal to a difference between the two currents output by the positive and negative current sources 406 and 410. For example, if positive current source 406 actually outputs 50 microamps of current and negative current source 410 actually outputs negative 52 microamps of current, current generation circuit 402 may output two microamps of current having a negative charge.

Current source management facility 304 may measure this mismatch current in any of the ways described herein and use the measured mismatch current to calibrate one or both of current sources 406 and 410. For example, in the example given above where the negative current source 410 actually outputs negative 52 microamps of current when it is supposed to output negative 50 microamps of current, an offset may be applied to the negative current source 410 so that its actual output current level matches its intended current level.

As another example, the systems and methods described herein may be used to determine an accuracy of a single current source (e.g., either positive current source 406 or negative current source 410). In this example, current source management facility 304 may direct cochlear implant 108 to enable the single current source for a time interval, which may be set to be any suitable duration. For purposes of this example, current source management facility 304 enables positive current source 406 for the time interval, while negative current source 410 remains disabled. In this scenario, the current output by current generation circuit 402 is the current output by positive current source 406.

In some examples, current source management facility 304 may enable positive current source 406 by providing a command to cochlear implant 108 for positive current source 406 to output a current having a specific current level during the time interval. Current source management facility 304 may measure the output current in any of the ways described herein and then compare the measured current level to the specific current level indicated in the command provided to cochlear implant 108. Based on this comparison, current source management facility 304 may calibrate positive current source 406 in any of the ways described herein.

To illustrate, stimulation management facility 302 may direct positive current source 406 to generate a positive current having a current level of 100 microamps. If current source management facility 304 determines that the actual level of current output by positive current source 406, for example, is less than 100 microamps (e.g., 98 microamps), current source management facility 304 may calibrate positive current source 406 by directing positive current source 406 to increase its level of generated current (e.g., by an increase of approximately two percent). In some examples, this calibration process may be an iterative process that includes multiple calibration attempts before the intended and actual levels of generated current are within a certain tolerance.

Figure 6:
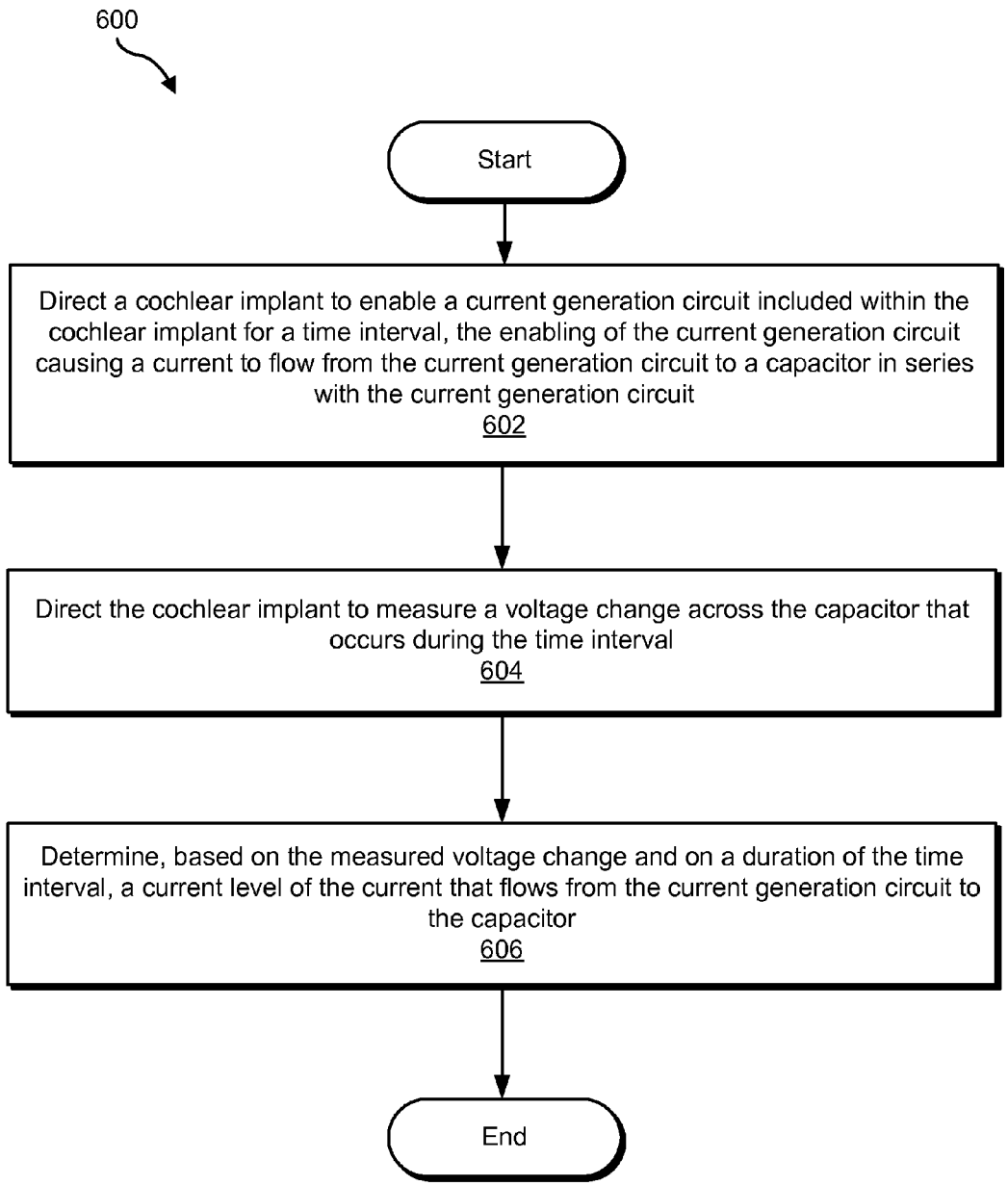
FIG. 6 illustrates an exemplary method for measuring a current output by a current generation circuit included in a cochlear implant according to principles described herein.

FIG. 6 illustrates an exemplary method 600 for measuring a current output by a current generation circuit included in a cochlear implant. While FIG. 6 illustrates exemplary steps according to one embodiment, other embodiments may omit, add to, reorder, and/or modify any of the steps shown in FIG. 6. One or more of the steps shown in FIG. 6 may be performed by sound processor 104 and/or any implementation thereof.

In step 602, a sound processor (e.g., sound processor 104) directs a cochlear implant to enable a current generation circuit included within the cochlear implant for a time interval. As described above, the enabling of the current generation circuit may cause a current to flow from the current generation circuit to a capacitor in series with the current generation circuit. Step 602 may be performed in any of the ways described herein.

In step 604, the sound processor directs the cochlear implant to measure a voltage change across the capacitor that occurs during the time interval. Step 604 may be performed in any of the ways described herein.

In step 606, the sound processor determines, based on the measured voltage change and on a duration of the time interval, a current level of the current that flows from the current generation circuit to the capacitor. Step 606 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sound processor; and
a cochlear implant communicatively coupled to the sound processor, the cochlear implant including
a current generation circuit,
a capacitor in series with the current generation circuit, and
a voltage measurement circuit;
wherein the sound processor
directs the cochlear implant to enable the current generation circuit for a time interval, the enablement of the current generation circuit causing current to flow from the current generation circuit to the capacitor during the time interval,
directs the cochlear implant to use the voltage measurement circuit to measure a voltage change across the capacitor that occurs during the time interval, and
determines, based on the measured voltage change and on a duration of the time interval, a current level of the current that flows from the current generation circuit to the capacitor.

2. The system of claim 1, wherein:
the current generation circuit comprises a positive current source and a negative current source;
the sound processor directs the cochlear implant to enable the current generation circuit for the time interval by directing the cochlear implant to concurrently enable the positive and negative current sources during the time interval; and
the current that flows from the current generation circuit to the capacitor during the time interval is a mismatch current that results from the positive and negative current sources being mismatched.

3. The system of claim 1, wherein the current generation circuit comprises a single current source that outputs the current while the current generation circuit is enabled.

4. The system of claim 3, wherein the sound processor provides a command to the cochlear implant for the single current source to output a current having a specific current level during the time interval.

5. The system of claim 4, wherein the sound processor:
compares the current level of the current that flows from the current generation circuit to the capacitor to the specific current level; and
calibrates the single current source based on the comparison.

6. The system of claim 1, wherein:
the capacitor comprises a first side coupled to an output of the current generation circuit and a second side coupled to a reference voltage level; and
the voltage measurement circuit includes a differential amplifier that measures the voltage change across the capacitor by determining a difference between a voltage level on the first side and a voltage level on the second side.

7. The system of claim 6, wherein the voltage measurement circuit further comprises an analog-to-digital converter coupled to an output of the differential amplifier and that converts the measured voltage change into a digital word representative of the measured voltage change.

8. The system of claim 7, wherein:
the cochlear implant further comprises communication circuitry that transmits the digital word representative of the measured voltage change to the sound processor; and
the sound processor determines the current level using the digital word.

9. The system of claim 1, wherein the cochlear implant further comprises:
a multiplexer that is positioned in series between the current generation circuit and the capacitor and that comprises a plurality of switches including a first switch associated with the current generation circuit and a second switch associated with the capacitor; and
wherein the sound processor directs the cochlear implant to close the first and second switches so that the first and second switches are closed during the time interval in order to allow the current to flow from the current generation circuit to the capacitor.

10. The system of claim 9, wherein the sound processor directs the cochlear implant to open at least one of the first and second switches upon completion of the time interval.

11. The system of claim 1, wherein the sound processor determines the current level of the current that flows from the current generation circuit to the capacitor in accordance with c*dv/dt, where c is a value of the capacitor, dv is the measured voltage change, and dt is the duration of the time interval.

12. The system of claim 1, wherein the sound processor uses the determined current level of the current that flows from the current generation circuit to the capacitor to calibrate the current generation circuit.

13. A cochlear implant comprising:
a current generation circuit;
a capacitor in series with the current generation circuit; and
a voltage measurement circuit;
wherein the current generation circuit outputs a current for a time interval, the current flowing from the current generation circuit to the capacitor; and
wherein the voltage measurement circuit measures a voltage change across the capacitor that occurs during the time interval.

14. The cochlear implant of claim 13, further comprising communication circuitry that transmits data representative of the measured voltage change to a sound processor.

15. The cochlear implant of claim 13, wherein the current generation circuit comprises a positive current source and a negative current source, and wherein the current output by the current generation circuit is a mismatch current that results from the positive and negative current sources being mismatched.

16. The cochlear implant of claim 13, wherein the current generation circuit comprises a single current source that outputs the current while the current generation circuit is enabled.

17. The cochlear implant of claim 13, wherein:
the capacitor comprises a first side coupled to an output of the current generation circuit and a second side coupled to a reference voltage level; and
the voltage measurement circuit includes a differential amplifier that measures the voltage change across the capacitor by determining a difference between a voltage level on the first side and a voltage level on the second side.

18. The cochlear implant of claim 13, further comprising:
a multiplexer that is positioned in series between the current generation circuit and the capacitor and that comprises a plurality of switches including a first switch associated with the current generation circuit and a second switch associated with the capacitor;
wherein the cochlear implant closes the first and second switches to allow the current that is output by the current generation circuit to flow from the current generation circuit to the capacitor.

19. The cochlear implant of claim 13, wherein the voltage measurement circuit further comprises an analog-to-digital converter coupled to an output of the differential amplifier and that converts the measured voltage change into a digital word representative of the measured voltage change.

20. A method comprising:
directing, by a sound processor, a cochlear implant to enable a current generation circuit included within the cochlear implant for a time interval, the enabling of the current generation circuit causing a current to flow from the current generation circuit to a capacitor in series with the current generation circuit;
directing, by the sound processor the cochlear implant to measure a voltage change across the capacitor that occurs during the time interval; and
determining, by the sound processor based on the measured voltage change and on a duration of the time interval, a current level of the current that flows from the current generation circuit to the capacitor.

* * * * *